United States Patent [19]
Kretz

[11] 4,287,767
[45] Sep. 8, 1981

[54] ULTRASONIC SECTION SURFACE EXAMINATION EQUIPMENT

[75] Inventor: Carl Kretz, Zipf, Austria
[73] Assignee: Kretztechnik Gesellschaft m.b.H., Zipf, Austria
[21] Appl. No.: 93,049
[22] Filed: Nov. 13, 1979
[30] Foreign Application Priority Data
Jan. 25, 1979 [AT] Austria .................. 522/79
[51] Int. Cl.³ .......................... G01N 29/00
[52] U.S. Cl. ...................... 73/625; 73/628; 128/660
[58] Field of Search ........ 73/618, 620, 625, 628, 73/629, 632, 633, 634, 641; 128/660

[56] References Cited
U.S. PATENT DOCUMENTS

| | | | |
|---|---|---|---|
| 3,605,724 | 9/1971 | Flaherty | 128/661 |
| 3,693,414 | 9/1972 | Soldner | 73/620 |
| 3,778,756 | 12/1973 | Houston et al. | 73/607 |
| 4,084,582 | 4/1978 | Nigam | 73/629 |
| 4,102,204 | 7/1978 | Kretz | 73/626 |
| 4,177,679 | 12/1979 | Soldner | 73/625 |
| 4,228,687 | 10/1980 | Fraser | 73/628 |

*Primary Examiner*—Stephen A. Kreitman
*Attorney, Agent, or Firm*—Kurt Kelman

[57] ABSTRACT

A scanning unit comprises two sound transducer heads for projecting sound beams, which are caused to scan a common section plane. Echo signals are derived from the echoes generated in response to said sound beams and are displayed on a fluorescent screen at locations which are geometrically coordinated with the locations at which the corresponding echoes have originated. The sound beam from one sound transducer head scans the section surface in an area which is generally rectangular or has only slightly divergent side edges. The sound beam from the other sound transducer head scans the section surface in an area which has greatly divergent side edges. These areas of the section surface are displayed on different areas of the fluorescent screen. Such scanning unit can be adapted to object of various shapes.

20 Claims, 4 Drawing Figures

ULTRASONIC SECTION SURFACE EXAMINATION EQUIPMENT

This invention relates to ultrasonic surface examination equipment comprising a scanning unit which includes at least two sound transducers for projecting sound beams and for receiving echoes produced in response to said sound beams and for converting them into echo signals, a scanning mechanism which is adjustable to a preselected section surface of an object to be examined and comprises mechanically movable members for moving the sound beams in the section surface, and display means for displaying said echo signals on a fluorescent screen at locations which are geometrically coordinated with the locations at which the corresponding echoes have originated.

If such ultrasonic equipment is operated at sufficiently high scanning frequency and picture frequency, it can be used also for a display of moving section images, so-called real-time displays. Two different methods have previously been employed for such displays and differ mainly in the nature of the movement of the sound beam is moved in the object and in the manner in which said movement is imparted. In the parallel-scan method the sound beam is moved to parallel positions at a velocity wich is as uniform as possible so that scanning is effected with a substantially uniform transverse resolution. For a parallel scan, sound transducer heads have been used which comprise a plurality of sound transducers, which are activated in succession individually or in groups. The transverse resolution of the scanning effected with such sound transducer heads is relatively low and they are mentioned here only for the sake of completeness. When equipment of the present kind is used, in which the sound beam is moved by mechanically moved members, the sound beam has in most cases been indirectly projected into the object. For this purpose a rotating sound transducer head has been arranged at or near the focus of a parabolic reflector, which is open toward the object, and the sound head has been activated as it moves past the reflector and projects the beam on the side remote from the object onto the reflector, by which the sound beam has been then reflected into the object. In order to avoid ghost echoes, the distance travelled by the beam before entering the object, i.e., the distance from the activated sound transducer of the sound transducer head to the reflector and from the latter to the point of entry into the object must always exceed the depth to which the sound penetrates the object. The sound transducer head may be provided with two sound transducers, which may have different foci and can be selectively used in dependence on the desired depth of penetration and other selected parameters.

For a parallel scan, the scanning unit must be in sound-transmitting contact with the object being examined throughout the width of the region which is to be displayed. It is often impossible to fulfill that requirement or to fulfill that requirement completely. Moving section images are particularly interesting for an examination of living beings, especially in human medical diagnosis. In many cases, that portion of the human body which is to be examined is so strongly curved that the sound-transmitting contact cannot be maintained throughout the width of the section surface. In medical examinations, consideration must also be given to the so-called sound windows which exist in the body and are required for an introduction of sound. Such sound windows exist, e.g., between the ribs. If the scanning movement is transverse to the ribs, only the spaces between the ribs will be displayed.

The second conventional method is sector scanning. In that method the sound transducer head is oscillated about an axis which lies approximately in the sound-emitting surface of the scanning unit so that the sound beam scans in the body a generally triangular section surface and it is sufficient to establish virtually at one point. The fact that the section surface being scanned is triangular involves the disadvantage that an image in a width which is required for a reasonable observation can be derived only from a region which is disposed at a substantial depth and that owing to the strong divergence of adjacent sound beams the surface is scanned only with a low transverse resolution in the region which can well be observed. Besides, said transverse resolution decreases from the vertex of the triangle towards its base and this lowers not only the accuracy of the display but also the brightness of the image.

In a compromise between parallel scanning and sector scanning, the sound beam is directly projected into the object being examined and the sound transducer head is pivotally moved about an axis which is spaced from the object so that a generally trapezoidal section surface is scanned. Compared to parallel scanning, this practice affords the advantage that the sound beam is directly projected into the object and that a smaller contact area is sufficient. Compared to the sector scanning of a triangular section surface, the area which can be observed is greatly increased and a sufficiently wide image is obtained also from a region that is closely below the surface. Besides, scanning is effected with a more uniform transverse resolution. In such equipment disclosed in U.S. Pat. No. 4,102,204, a wheel is used, which is provided at its periphery with a plurality of sound transducers, each of which is activated as it moves past a window, which is provided in the housing of the scanning unit and faces the object.

It is an object of the invention to provide ultrasonic equipment which can be almost universally adapted to the coupling capabilities of the object to be examined and can be used for an examination under conditions which are optimum in each case.

This object is accomplished in that the scanning unit comprises first and second transducer heads, each of which comprises at least one sound transducer for a projecting at least one of said sound beams, said scanning mechanism is operable to cause at least one sound beam from the first sound transducer head to scan the section surface in a first area, which is generally rectangular or has only slightly divergent side edges, said scanning mechanism is operable at the same time to cause at least one sound beam from said second sound transducer head to scan the section surface in a second area in a movement which is coordinated and preferably synchronized with the movement of said at least one beam from said first sound transducer head, which second area is adjacent to said first area and has highly divergent side edges, said display means are adapted to display at the same time on said fluorescent screen the echo signals derived from the scanning of the section surface with the sound beams from both said sound transducer heads in respective component images.

As a result of the arrangement which has been described, the center lines of the component images derived from the two sound transducer heads include an angle with each other and the scanning unit housing of which contains the sound transducer heads can be provided with a surface which is adapted to contact the object and which has a substantially plane or only slightly curved surface portion for parallel scanning and an adjoining surface portion which is strongly curved or at an angle to the first-mentioned surface portion and is used for sector scanning. The housing can be urged, e.g., against soft parts of the human body, such as the upper part of the abdomen, in such a manner that the sector scan will cover regions under the costal arch. The upper edge of the area covered by the sector scan may include only a very small angle with the contact surface for parallel scanning and may be even parallel to said surface. For an examination of strongly curved portions of the body, the housing may be inclined so that at least the contact surface for sector scanning contacts the body. Change-over switches may be optionally provided, which cause only the sound transducer or transducers of one sound transducer head to be operated. In most cases, however, both sound transducer heads will always be operated and the scanning unit housing will be adjusted on the body in an attempt to obtain a favorable coupling. Any regions in which there is no proper coupling will remain blank in the section display.

If a portion of a section surface having divergent edges is covered by a parallel scan or quasiparallel scan, the largest angle of divergence between the side edges of the area covered by the sound beam in that portion of the section surface will be as large as or smaller than one-half of the angle of divergence between side edges of the other portion.

The requirement of a simultaneous display of the adjoining areas of the section surface can be exactly fulfilled only when it is ensured that at least the one sound beam projected by each sound transducer head can actually reach the boundary region between the two areas being scanned. To ensure that the requirement will be exactly fulfilled, that boundary region must be cleared by the at least one sound beam projected from a given sound transducer head when said boundary region is being scanned by the other sound transducer head. In order to meet this requirement, an arrangement is preferably selected in which the scanning unit defines for a sound beam from one sound transducer head a sound path portion of negligibly small length outside the object to be examined and defines for the sound beam from the other sound transducer head, preferably for the sound beam for scanning the area having less divergent or substantially parallel side edges, a sound path portion of substantial length outside the object to be examined, because in that case the sound can be so deflected that only the first-mentioned sound transducer head moves actually over the boundary portion between the two areas adjacent to the contact surface. In that case, that sound transducer head must be clear in at least one predetermined operating position of an adjacent marginal area of the range of movement of said sound path portion of substantial length disposed outside the object to be examined.

To ensure that the scanning unit, which constitutes the means to be handled by the examinator, has only a small overall height, an arrangement may be adopted in which at least one reflector for directing the at least one sound beam from said one sound transducer head to a sound exit window of the scanning unit is arranged in the sound path portion of substantial length disposed outside the object, and the scanning mechanism is operable to impart a preferably oscillating movement to said one sound transducer head and/or said reflector in order to move the sound beam in the associated area of the section surface. The reflector may be curved, or a plurality of reflectors may be provided so that the space traversed by the sound before entering the object can be further decreased.

When a continuous transition between the areas of the section surface is not required even near the surface of the object, the two areas may have overlapping divergent edges and said edges may be spaced apart close to the housing of the scanning unit so that the associated edges of the areas intersect within the object. In that case the requirement that one sound transducer head must be clear even within the scanning unit of the range in which the at least one sound beam from the other sound transducer head is moved adjacent to the boundary region need not be met. The display means may be so arranged that the boundary region is represented in the display only by the signals which belong to one component image.

According to a preferred further feature, the sound transducer heads or one sound transducer head and the reflector associated with the other sound transducer head are adapted to be mechanically driven to oscillate in phase quadrature and the associated sound transducers are controlled by switches to be activated only during those portions of the period of oscillation in which the velocity at which the associated sound beams scan the section surface is approximately constant so that scanning is effected with a substantially uniform transverse resolution in spite of the oscillating movement.

Various measures may be adopted to show both component section images as a total section image. If scanning can be performed at a sufficiently high frequency, the two sound transducers can be operated in alternation, e.g., with line alternation, so that the two section images are traced by a beam which moves over the fluorescent screen in unison with the movement of the associated sound beam in the object being examined. A simplified display, e.g., by means of a television monitor, will be achieved, if buffer memory means are provided, writing control means are provided for writing the echo signals from said sound transducer heads into the memory means at addresses coordinated with the locations at which the corresponding echoes have originated, and reading means are provided for reading the stored signals at the addresses in accordance with a predetermined program in a sequence which may differ from the sequence in which the signals have been written into the memory means, and for delivering the read signals to means for controlling the display on the fluorescent screen.

During examinations of the heart, eight complete scans per second are normally sufficient for a significant moving section image. When that scanning frequency is adopted, the sound transducer head from which the sound travels over a substantial distance before entering the object can also be operated at a pulse repetition frequency which is sufficiently high for scanning with a sufficiently fine transverse resolution. In order to avoid a time jitter of the image, the temporary storage may be effected by means of an overwriting memory which can be read several times, and the reading frequency may be a multiple of the frequency at which the sound beams scan the section surface.

If the sound beam which travels over a distance before entering the object is to scan at the highest possible frequency and the scanning with that sound beam should not be interrupted for a change-over to the other sound transducer head, the sound transducers of both sound transducer heads may be activated by the same control pulse or by means of control pulses triggered at the same time at the highest pulse repetition frequency which is permissible for the sound beam which travels through a distance before entering the object, and timed change-over switches or gating circuits may be provided, which are triggered by the control pulses to connect the sound transducer head associated with the sound path portion of negligibly small length disposed outside the object and subsequently the sound transducer head associated with the sound path portion of substantial length disposed outside the object to the control means or the writing control means. Such an arrangement will be interesting if the position of the two sound beams is such that the operation of each sound transducer head during the time in which it is conditioned to receive echoes will not be influenced by the operation of the other sound transducer head.

If the sound transducer heads are activated periodically in alternation and a scanning with the highest possible accuracy is desired, the directly coupled sound transducer head may be moved at a higher scanning frequency than the other sound transducer head if a switch is provided which changes the pulse repetition frequency at each change-over from one sound transducer head to the other.

Further details and advantages of the subject matter of the invention will become apparent from the following description of the accompanying drawings, in which the subject matter of the invention is shown by way of example.

Figure 1:
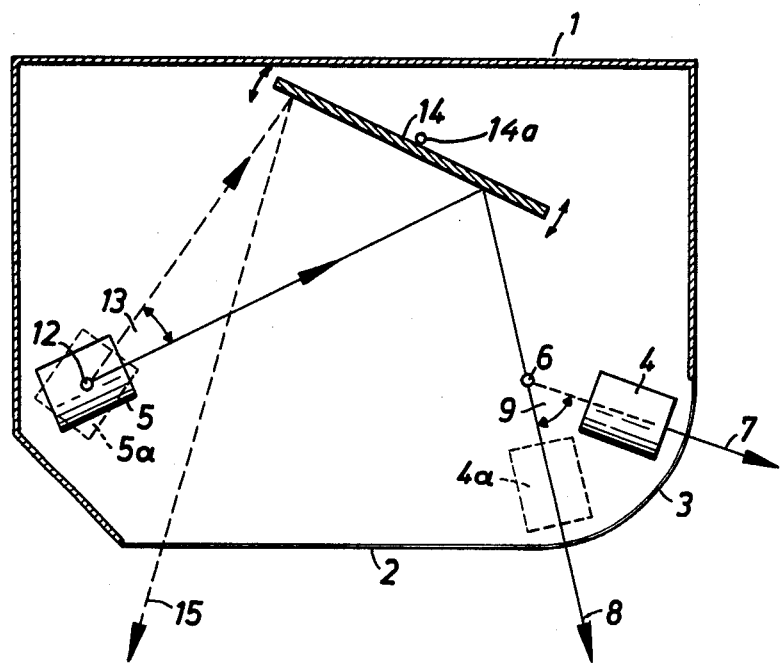
FIG. 1 is a highly diagrammatic sectional view showing a scanning unit of equipment according to the invention.
Figure 2:
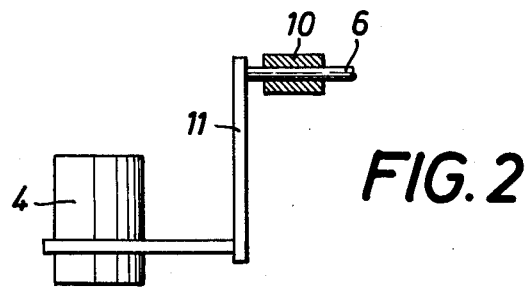
FIG. 2 shows as a detail of FIG. 1 the means for moving one sound transducer head.

In the embodiment shown in FIG. 1, all acoustic components of a scanning unit are accommodated in a housing 1, which is filled with a sound-conducting liquid and has on its underside a sound exit window 2, 3, including a flat portion 2, which in the present embodiment is longer, and a curved portion 3, which adjoins the flat portion 2. Two sound transducer heads 4, 5 are accommodated in the house 1. The sound transducer head 4 is pivoted on a pivot 6, which is spaced from the curved portion 3 of a window, so that the sound transducer of the sound transducer head 4 slides over the sound window 3 and the sound beam projected by the head 4 is moved between end positions 7 and 8 to scan a section surface in an area which has highly divergent side edges. The sound transducer head 4 is shown in solid lines in one end position and in dotted lines in the other end position at 4a. A usual angle 9 between the directions of the sound beam in the two end positions 7 and 8 may be 60 to 70 degrees. As is apparent from FIG. 2 the sound transducer head 4 is secured by a crank 11 to the pivot 6, which is mounted in a bearing 10 and is laterally offset from the sound transducer head 4.

The second sound transducer head 5 is adapted to be pivotally oscillated about a pivot 12 and is again shown in one end position with solid lines and in the other end position at 5a with dotted lines. In the embodiment shown by way of example, the angular range 13 of the pivotal movement is one-half of the angular range 9 of the pivotal movement of the sound transducer head 4. The axis of the sound beam projected by the sound transducer head 5 extends to a reflector 14. The reflector may also be oscillated about pivot 14a and during a pivotal movement of the sound transducer head 5 or reflector 14, the sound beam projected by the head 5 moves substantially between the end positions 8 and 15 in scanning the associated area of the section surface in the object to be examined. The angle of divergence of directions 8 and 15 is as large as or smaller than one-half of the angle of divergence of directions 7 and 8. As the inclination of the direction 7 from the plane of the portion 2 of the sound exit window is very small, the sound beam projected by the sound transducer head 4 can scan an object to be examined also in a region which is disposed laterally of and above the window 2 if the housing 1 is urged to some extent into the object. The two sound transducer heads 4 and 5 are driven by a motor, which is disposed outside the housing 1, by means of intermediate transmissions, which are not shown for the sake of clearness and consist of crank drives having different transmission ratios. The motions of the heads 4 and 5 are so coordinated with each other that the sound beam projected by the sound transducer head 5 will assume the position 8 only when the corresponding sound beam path in the housing 1 has been cleared by the sound transducer head 4. It will be endeavored to ensure that the two sound transducer heads 4 and 5 never assume a position in which a sound beam projected by one of them may give rise to echoes which influence the other sound transducer head. In specific cases, only one of sound transducer heads may be moved at a time and a pulse generator may be controlled by a change-over switch to activate only the sound transducer head which is moving at a given time so that only that section surface area which is scanned by said sound transducer head is displayed. When the two sound transducer heads 4 and 5 are operated at the same time and the scanned areas of the section surface are displayed, a separate pulse generator and a separate receiver may be associated with each sound transducer head and the cathode ray tube may consist of a two-beam tube in which a separate electron beam is associated with each sound transducer head, or a memory and an address computer may be associated with each sound transducer head. In the latter case, the echo signals delivered by each sound transducer head will be stored at addresses coordinated with the locations at which the corresponding data have originated and possibly so as to indicate a proper intensity parameter and a reading computer will be used to periodically read the memories and to cause the signals generated by the two sound transducer heads to be displayed at the same time. The address at which a memory is being read will also control the deflecting voltage for the display on the fluorescent screen and the intensity parameter will control the brightness of the display. Signals indicating the addresses for the storage of each echo signal will be generated by the scanning mechanism for moving the sound transducer heads in accordance with the respective position of the respective sound transducer head, specifically by pick-ups which are mounted on the motor, the transmission or directly on the sound transducer heads 4, 5 or their pivots 6, 12. These signals are processed together with a sweep sawtooth voltage which is synchronized with the control pulses applied to the sound transducer and constitutes a measure of the delay of each echo. The memories may be read during the flyback of the sawtooth voltage. Reading can be accomplished within a time that is much shorter than the time which must be allowed for writing because the latter time must be determined in accordance with the longest delay to be expected for the echoes. For a trouble-free operation, a simultaneous reading of the two memories should be possible. For this purpose the pulse generators which control the two sound transducer heads are controlled by the same clock so that the addresses for both memories can be derived from the same sawtooth voltage and the same time is allowed for reading both memories during the flyback of said sawtooth voltage.

Because the sound beam projected by the sound transducer head 5 travels over a distance before entering the object, the scanning rate which can be achieved at least with that sound transducer head is lower, in theory, than the scanning rate which can be effected with the sound transducer head 4, which projects sound directly into the object. Nevertheless, about 8 scans per second can be effected even with the sound beam from the sound transducer head 5 and this will be sufficient for a display of motions inside the human body. To prevent a flutter on the fluorescent screen both memories are read two or more times whenever an image has been written into them so that the usual picture frequency of about 20 to 30 pictures per second can be adopted.

If a simplification is desired, electronic change-over switches may be provided for connecting the two sound transducer heads 4 and 5 in alternation to the pulse generator and receiver at a high change-over frequency. In that case, only one memory is required and one address computer for writing into the memory because only signals from one sound transducer head can be received at a time. The address computer must be switched over in synchronism in that case so that it receives and processes at any time the signals which correspond to the instantaneous position of the activated sound transducer head.

Figure 3:
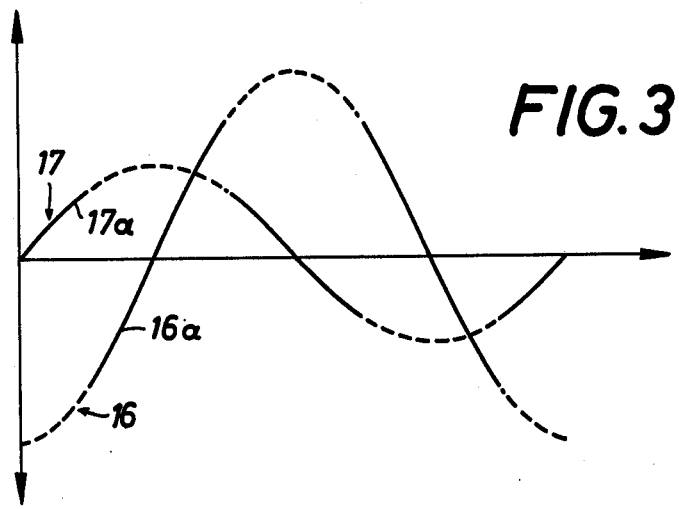
FIG. 3 is a velocity-displacement diagram for the sound beams projected by both sound transducer heads.

In order to avoid excessively large inertia forces, the two sound transducer heads 4 and 5 are preferably moved to perform a harmonic oscillating motion, such as is represented in FIG. 3 by the two sine curves 16, 17. In that case, the velocity of the angular movement of each sound transducer head will vary so that an activation of the sound transducer heads by control pulses having a constant pulse repetition frequency will cause the section surface to be scanned with a varying transverse resolution, which increases toward the side edge of the respective section surface area. The section surface can be scanned with a uniform transverse resolution if the central portion of each section surface area is scanned at a higher pulse repetition frequency and the side edge portions of said area are scanned at a lower pulse repetition frequency, or if each of the two sound transducer heads 4,5 is simply caused to oscillate through a larger angle than would be required to scan the associated area of the scanning surface. In the latter case, only the movements corresponding to the substantially linear portion 16a, 17a of curves 16, 17 in FIG. 3 are actually used for scanning; these portions correspond to a substantially constant angular velocity of the sound beams. Also with reference to FIG. 3, the motions of the two sound transducer heads 4 and 5 may be performed in phase quadrature so that each sound transducer head will perform the movement at constant angular velocity during a time in which the angular velocity of the other sound transducer head changes rapidly. In such case the each sound transducer head may be activated only when it moves at constant angular velocity so that one of the two sound transducer heads is activated at any time and 100% of the time available will be utilized.

Figure 4:
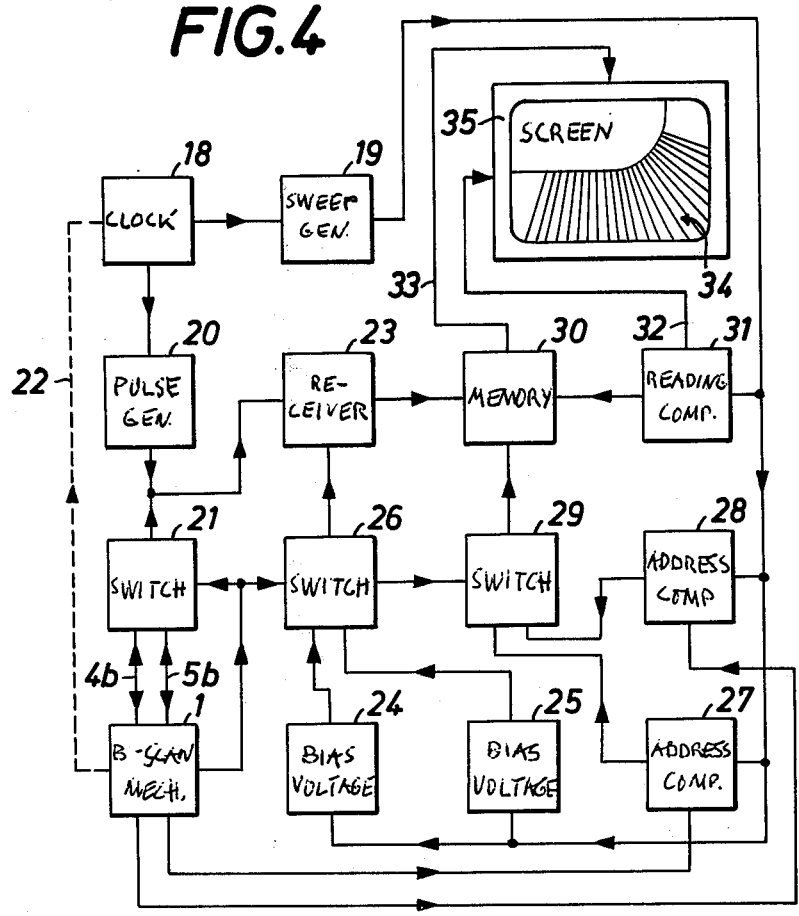
FIG. 4 is a block circuit diagram of equipment according to the invention.

The equipment represented by a block circuit diagram in FIG. 4 comprises a clock 18, which triggers a sweep generator 19 and a pulse generator 20. The control pulses generated by the pulse generator 20 are delivered to an electronic change-over switch 21 and are applied by the latter via leads 4b, 5b to the two sound transducer heads 4, 5 of the scanning unit 1. The change-over is controlled in accordance with the timing represented in FIG. 3. The Change-over switch 21 is controlled by the scanning unit 1 in dependence on the instantaneous position of the sound transducer heads 4, 5. Because the sound beam 4 projects sound directly into the object, a higher pulse repetition frequency may be adopted when this sound transducer head is activated. For this purpose, the clock 18 may be controlled by the scanning unit 1 via a lead 22, indicated by a dotted line, to operate at a higher clock frequency when the sound transducer head 4 is activated. Whether or not this measure is adopted, the further processing will be effected in the manner which will be described hereinafter.

The echo signals generated by the sound transducer head 4 or 5 which is activated are delivered to the change-over switch 21, which forwards them to a receiver 23, which constitutes that part of the equipment in which the echo signals are processed. This processing of signals includes amplifying, demodulating, filtering, threshold control and depth compensation. Depth compensation is effected by two bias voltage generators 24, 25, which are repeatedly triggered by the sweep generator 19 to generate a time-base bias voltage. Different generators 24, 25 are required because the section images derived from the sound transducer heads 4, 5 represent different depth portions of the sound fields of said heads so that different depth compensations are required. An electronic change-over switch 26 is also controlled by the scanning unit 1 and connects that voltage generator 24 or 25 to the receiver which is associated with the activated sound transducer head.

For each of the two sound transducer heads, an address computer 27 or 28 is provided, which receives from the scanning unit 1 a position signal indicating the position of the activated sound transducer head, and receives from the sweep generator 19 a sawtooth voltage, and in dependence on said position signal and sawtooth voltage determines addresses associated with respective echoes which are received. The outputs of the two address computers 27, 28 are connected to another change-over switch 29, which is also controlled by the scanning unit 1 and connects the address computer which is associated with the activated sound transducer head to the memory 30, in which the echo signals from the receiver 23 are stored at the indicated addresses. The sweep generator 19 controls also a reading computer 31, which during each flyback of the sawtooth voltage is activated to read the contents of the memory 30 in accordance with a program which may be highly independent of the sequence in which the echo signals have been written into the memory 30. By means of the lead 32, the reading program controls the deflection of the electron beam in the cathode ray tube and of the light spot on the fluorescent screen 35. The intensity signals derived from the storage locations of the memory 30 are transmitted via lead 33 and used for brightness control. In this way, a complete picture 34 is traced on the fluorescent screen 35 between successive control pulses and the picture frequency on the fluorescent screen greatly exceeds the frequency at which the results of successive complete scans of the section surface are written into the memory 30.

It has been mentioned hereinbefore that the sound transducer head 5 may be stationary and the reflector 14 may be driven to oscillate instead of or in combination with the sound transducer head 5. The angular range of the partial section image derived from the sound transducer head 5 might be modified by a curvature of the reflector 14 so that smaller pivotal movements of the sound transducer head 5 may be sufficient and the inertial forces are thus reduced. Change-over switches may be provided which can be controlled so that only one of the two sound transducer heads 4 and 5, as desired, is mechanically driven, whereas the other sound transducer head is held in a position in which it does not interfere with the operation of the sound transducer head which is mechanically driven, or, that both sound transducer heads are mechanically driven but only one of them is activated. When one sound transducer head is disabled, the change-over switches 21, 26 and 29 will be held in the position associated with the activated sound transducer head. The two sound transducer heads 4 and 5 may be different in design from the embodiment which has been shown. Specifically, the sound transducer head 5 may be disposed in the scanning unit at different locations and the sound beam projected by the head 5 may be deflected several times by a plurality of reflectors. A sound transducer head may comprise two sound transducers, which project sound beams along axes that include an angle with each other, and these sound transducers may be activated in alternation. Such sound transducer head requires only a smaller angular movement. Arrangements comprising rotating sound transducer heads or, at least for a parallel scan, arrangements comprising sound transducer heads which reciprocate along a straight line along the sound window 4, may also be adopted. The invention covers also equipment comprising more than one sound transducer head for scanning the section surface in an area which has substantially divergent side edges and/or at least one sound transducer head for scanning the section surface in an area which has only slightly divergent or substantially parallel side edges.

What is claimed is:

1. Ultrasonic section surface examination equipment, comprising
    a scanning unit which defines a plurality of sound paths and comprises first and second sound transducer heads, each of which comprises at least one sound transducer that is operable to project a sound beam along an associated one of said sound paths into a section surface of an object to be examined and to receive echo signals generated in said section surface in response to said sound beam and to derive echo signals from the echoes thus received,
    scanning mechanism means for mechanically operating said scanning unit so as to move said sound paths transversely to themselves in said section surface in coordinated movements whereby the sound beam projected from a sound transducer of said first sound transducer head is caused to scan said section surface in a first section surface area having substantially divergent side edges and the sound beam projected from a sound transducer of said second sound transducer head is caused to scan said section surface in a second section surface area which is adjacent to said first area and has side edges which are less divergent than those of said first area, and
    display means comprising a fluorescent screen and operable to display said echoes on said fluorescent screen in response to echo signals from said sound transducer of said first sound transducer head in a first screen area at locations which are geometrically coordinated with the locations at which the corresponding echoes have originated in said first section surface area and, at the same time, in response to echo signals from said sound transducer of said second sound transducer head in a second screen area at locations which are geometrically coordinated with the locations at which the corresponding echoes have originated in said second section surface area.

2. Equipment as set forth in claim 1, in which said scanning mechanism means are operable to impart synchronized movements to said sound paths.

3. Equipment as set forth in claim 1, in which said scanning mechanism means are operable to mechanically operate said scanning unit so that the section surface area scanned by said sound beam projected by said sound transducer of said second sound transducer head has substantially parallel side edges.

4. Equipment as set forth in claim 1, in which
    said scanning mechanism means are operable to move said sound beam projected from said sound transducer of said first sound transducer head between end positions defining said side edges of said first section surface area and including a first angle of divergence and to move said sound beam projected from said sound transducer of said second sound transducer head between end positions defining said side edges of said second section surface area and including a second angle of divergence which is not in excess of one-half of said first angle of divergence.

5. Equipment as set forth in claim 1, in which
    said scanning unit comprises a sound exit for contacting said object at said section surface and
    said scanning unit defines a first sound path having a portion of substantial length from said sound transducer of one of said sound transducers to said sound exit and
    said scanning unit defines a second sound path having a portion of negligible length from said sound transducer of the other of said sound transducer heads to said sound exit.

6. Equipment as set forth in claim 5, in which said one sound transducer head is said second sound transducer head.

7. Equipment as set forth in claim 5, in which
    said scanning mechanism is operable to move said portion of substantial length through a predetermined range in order to scan said section surface with said first sound path in one of said first and second areas, said scanning mechanism is operable to move said other sound transducer head in order to scan said section surface with said second sound path in the other of said areas, and the arrangement is such that said other sound transducer head is clear of said predetermined range at least in one position of said other sound transducer head.

8. Equipment as set forth in claim 5, in which
said scanning unit comprises a reflector for deflecting said first sound path to said sound window.

9. Equipment as set forth in claim 8, in which said scanning mechanism means are operatively connected to said one sound transducer head and operable to move said sound transducer head in order to move said first sound path transversely to itself in said section surface.

10. Equipment as set forth in claim 9, in which said scanning mechanism means are operable to oscillate said one sound transducer head.

11. Equipment as set forth in claim 8, in which said scanning mechanism means are operatively connected to said reflector and operable to move said reflector in order to move said first sound path transversely to itself in said section surface.

12. Equipment as set forth in claim 11, in which said scanning mechanism means are operable to oscillate said reflector.

13. Equipment as set forth in claim 8, in which said scanning mechanism means are operatively connected to said first sound transducer head and to said reflector and operable to move said first sound transducer head and said reflector in order to move said first sound path transversely to itself in said section surface.

14. Equipment as set forth in claim 13, in which said scanning mechanism means are operable to oscillate said one sound transducer head and said reflector.

15. Equipment as set forth in claim 5, in which
pulse generator means are provided, which are operable to generate a series of control pulses, said sound transducers of both said sound transducer heads are arranged to receive said control pulses at the same time and to project said sound beams in response to said control pulses, and switching means are provided, which are arranged to be triggered by said control pulses and in response thereto to deliver said echo signals from said other sound transducer head and subsequently said echo signals from said one sound transducer head to said display means.

16. Equipment as set forth in claim 15, in which said pulse generator means comprises
two pulse generators, each of which is adapted to deliver a control pulse to one of said sound transducer heads in response to a trigger pulse, and
triggering means for delivering trigger pulses to both said pulse generators at the same time.

17. Equipment as set forth in claim 15, in which said switching means comprise
change-over switch means for alternatively connecting said two sound transducer heads for a delivery of said echo signals to said display means, and
timing means for controlling said changeover switch means in response to said control pulses.

18. Equipment as set forth in claim 15, in which said switching means comprise
gating circuit means for selectively connecting each of said sound transducer heads for a delivery of said echo signals to said display means, and
timing means for controlling said gating circuit means in response to said control pulses.

19. Equipment as set forth in claim 1, in which
said scanning mechanism means are operable to oscillate said sound beam projected by said sound transducer from said first sound transducer head and said sound beam projected by said sound transducer of said second sound transducer head with a phase displacement of 90° and in such a manner that each of said sound paths is moved transversely to itself at a substantially constant velocity during at least one part of its period of oscillation and
switch means are provided for activating each of said sound transducers only during said at least one part of the period of oscillation of the associated sound path.

20. Equipment as set forth in claim 1, in which said display means comprise
buffer memory means,
write control means for writing said echo signals from said sound transducer heads into said memory means at locations coordinated with the locations at which the corresponding echoes have originated,
program-controlled reading means for reading said echo signals at said addresses in a program controlled sequence, and
displayed control means for controlling the display on said fluorescent screen in accordance with the echo signals thus read.

* * * * *